US011247075B2

(12) United States Patent
Chen et al.

(10) Patent No.: US 11,247,075 B2
(45) Date of Patent: Feb. 15, 2022

(54) ULTRASONIC PROBE DEVICE

(71) Applicant: Industrial Technology Research Institute, Hsin-Chu (TW)

(72) Inventors: Chun-Jung Chen, Hsinchu County (TW); Kun-Ta Wu, Nantou County (TW); Chia-Pin Li, Taichung (TW)

(73) Assignee: INDUSTRIAL TECHNOLOGY RESEARCH INSTITUTE, Hsin-Chu (TW)

( * ) Notice: Subject to any disclaimer, the term of this patent is extended or adjusted under 35 U.S.C. 154(b) by 395 days.

(21) Appl. No.: 16/228,938

(22) Filed: Dec. 21, 2018

(65) Prior Publication Data
US 2020/0196982 A1     Jun. 25, 2020

(51) Int. Cl.
*A61B 90/50*      (2016.01)
*A61N 7/02*       (2006.01)
(Continued)

(52) U.S. Cl.
CPC .............. *A61N 7/02* (2013.01); *G10K 11/355* (2013.01); *A61N 2007/0008* (2013.01); *A61N 2007/0091* (2013.01)

(58) Field of Classification Search
CPC .............. A61N 7/00; A61N 2007/0091; A61N 2007/0008; A61N 7/02; A61B 8/4218; A61B 8/4444; A61B 34/20; A61B 2034/2046; A61B 90/50; A61B 8/4461; G01S 7/52079; G10K 11/352; G10K 11/355; G01N 29/225; G01N 29/265
See application file for complete search history.

(56) References Cited

U.S. PATENT DOCUMENTS 7,133,713 B2    11/2006   Zan
7,635,335 B2    12/2009   Hwang
(Continued)

FOREIGN PATENT DOCUMENTS

CN        1461942 A     12/2003
CN     203802492 U      9/2014
(Continued)

OTHER PUBLICATIONS

TW OA issued on Jan. 13, 2020.

*Primary Examiner* — Amanda Lauritzen Moher
*Assistant Examiner* — Remy C Cooper
(74) *Attorney, Agent, or Firm* — WPAT, PC

(57) ABSTRACT

An ultrasonic probe device includes a sealed housing, a spiral-track plate, a driving arm, an ultrasonic probe and a first shaft. The spiral-track plate, disposed inside the sealed housing, includes a pivotal hole and a spiral groove, in which the spiral groove is extended outward from a center of the spiral-track plate. The driving arm, adjacent to the spiral-track plate, includes a first slot and a rotational shaft hole. The ultrasonic probe includes a follower pillar, a detection side and a connection side opposing to the detection side. The follower pillar, connected with the connection side, penetrates through the first slot and enters the spiral groove. The spiral groove provides a planar motion track to the detection side of the ultrasonic probe. The first shaft orderly penetrates through the sealed housing, the pivotal hole of the spiral-track plate, and the rotational shaft hole of the driving arm.

30 Claims, 10 Drawing Sheets

(51) Int. Cl.
  *G10K 11/35*  (2006.01)
  *A61N 7/00*  (2006.01)

(56) References Cited

U.S. PATENT DOCUMENTS

| | | |
|---|---|---|
| 8,475,384 B2 | 7/2013 | Hart et al. |
| 2008/0214937 A1 | 9/2008 | Kim |
| 2009/0275836 A1 | 11/2009 | Fujii et al. |
| 2011/0071399 A1 | 3/2011 | Tang et al. |
| 2011/0201937 A1 | 8/2011 | Fujii et al. |
| 2012/0065515 A1 | 3/2012 | Sato et al. |
| 2014/0257145 A1 | 9/2014 | Emery |
| 2016/0220229 A1 | 8/2016 | Hasegawa et al. |
| 2016/0332006 A1* | 11/2016 | Slayton ............... G01S 15/8934 |
| 2018/0209944 A1 | 7/2018 | Naka |

FOREIGN PATENT DOCUMENTS

| | | | |
|---|---|---|---|
| CN | 104434220 A | 3/2015 | |
| CN | 107144641 A | 9/2017 | |
| CN | 207081698 U | 3/2018 | |
| DE | 2800681 A1 | 7/1978 | |
| KR | 20180089309 A * | 8/2018 | |
| TW | 201211530 A | 3/2012 | |
| TW | M524693 | 7/2016 | |
| TW | I621460 | 4/2018 | |
| TW | 201819905 | 6/2018 | |
| WO | WO-2013084093 A1 * | 6/2013 | ........... A61B 8/4254 |

\* cited by examiner

ULTRASONIC PROBE DEVICE

TECHNICAL FIELD

The present disclosure relates to an ultrasonic probe device.

BACKGROUND

The cosmetic surgery is a medical technique that utilizes medicines, instruments, surgeries and the like medical resorts. The medical technique modifies human's appearances, shapes, colors and some physiological functions so as to increase people's aesthetic feeling. The cosmetic surgery is mainly grouped into invasive cosmetic procedures (plastic surgeries) and non-invasive cosmetic procedures (micro plastic surgeries). The invasive cosmetic procedures include nose augmentation, eye plastic and the like cosmetic surgeries. The noninvasive cosmetic procedures include lifting, lipolysis, and the like non-surgeries treatments.

As progress in technology, various innovative techniques have been introduced to the cosmetic surgery. By having a probe for the HIFU (High intensity focused ultrasound) as an example, the HIFU probe energized by ultrasound is usually applied onto the skin. By providing penetrability and focusability, the HIFU probe would emit an ultrasonic-wave energy to be focused at the subcutaneous fat layer. Obviously, in this technique, the ultrasonic wave of this technique would reach deep into the skin so as to be precisely focused under the skin. Such a technique is non-invasive, radiation-free, and applicable to lifting or lipolysis, and thus can firm the skin and eradicate deep or shallow fat.

While the HIFU probe is applied for lifting, lipolysis or the like cosmetic surgery, hundreds or thousands of points of ultrasonic-wave energy shall be applied within a planar block. Two application types of the conventional HIFU probe are usually seen. One application type is a line segment type, that is, one line segment is emitted and applied at a time. With the aforesaid linear-type application, then a 2D pattern within a planar block can only be obtained by plural back and forth moments. Namely, an operator shall move the probe frequently according to different line segments, which may have uneven movement pitch within the planar block. The other application type has a sensor formed as a soft protrusion, which is able to move on a curve surface and to produce a curved effective area. To perform an application with specific curvatures, a certain pressure shall be applied onto the skin so as to produce a planar block. However, while in pressing operation, the distance between the probe and the application target will be different. And thus, application depths in the center regions of the planar block will be different from application depths in the periphery regions of the planar block. In other words, such curved type and its sensor motion would contribute less to the uniformity of application depths over the planar block.

Thus, the topic for providing an improved ultrasonic probe device to lessen the aforesaid shortcomings is definitely urgent to the art.

SUMMARY

Accordingly, it is an object of this disclosure to provide an ultrasonic probe device that has a planar motion track for guiding an ultrasonic probe.

In one embodiment of this disclosure, the ultrasonic probe device includes a sealed housing, a spiral-track plate, a driving arm, an ultrasonic probe and a first shaft. The spiral-track plate is disposed inside the sealed housing, and the spiral-track plate includes a pivotal hole and a spiral groove, in which the spiral groove is extended outward from a center of the spiral-track plate. The driving arm is adjacent to the spiral-track plate, and the driving arm includes a first slot and a rotational shaft hole. The ultrasonic probe includes a follower pillar, a detection side and a connection side opposing to the detection side. The follower pillar is connected with the connection side, and the follower pillar penetrates through the first slot and enters the spiral groove. The spiral groove provides a planar motion track to the detection side of the ultrasonic probe. The first shaft orderly penetrates through the sealed housing, the pivotal hole of the spiral-track plate, and the rotational shaft hole of the driving arm.

In another embodiment of this disclosure, the ultrasonic probe device includes a sealed housing, a spiral-track plate, a gear, a rocker arm, an ultrasonic probe and a shaft. The spiral-track plate is disposed inside the sealed housing, and the spiral-track plate includes a pivotal hole and a spiral groove, in which the spiral groove is extended outward from a center of the spiral-track plate. The gear is adjacent to the spiral-track plate, and the gear has a first slot and a center pivotal hole. The rocker arm has one end thereof further having a pivotal shaft. The pivotal shaft is fixed to the sealed housing. The rocker arm has a second slot. The ultrasonic probe includes a follower pillar, a detection side and a connection side opposing to the detection side. The follower pillar is connected with the connection side, and the follower pillar penetrates through the first slot and the second slot and enters the spiral groove. The spiral groove provides a planar motion track to the detection side of the ultrasonic probe. The first shaft orderly penetrates through the sealed housing, the pivotal hole of the spiral-track plate, and the center pivotal hole of the gear.

As stated above, in the ultrasonic probe device of this disclosure, during the motion of the ultrasonic probe along the planar motion track inside the sealed housing, since the spiral groove provides the planar motion track for the detection side of the ultrasonic probe to follow, the ultrasonic probe thus can follow the planar spiral track to apply the ultrasonic-wave energy. In addition, the operator can apply ultrasonic-wave energy onto hundreds or thousands of application points within the planar block of the application target (for example, the subcutaneous fat layer of human body) without moving the ultrasonic probe device. And the distance between the ultrasonic probe device and the application target (for example, the subcutaneous fat layer of human body) is fixed. As such, better uniformity of the application depth of the applied ultrasonic-wave energy over the planar block can be obtained.

Further, in accordance with this disclosure, the ultrasonic probe, the spiral-track plate and the driving arm are disposed inside the sealed housing of the ultrasonic probe device provided. Further, through kinematic and connection relationships established by having the follower pillar to penetrate through slots (the first slot for example) and engage the spiral groove, the ultrasonic probe can apply ultrasonic-wave energy within the planar block with a certain depth.

In addition, the ultrasonic probe device of this disclosure can be arbitrarily replaced or assembled by related ultrasonic components so as to apply a specific planar block, and the associated replace ability and convenience of the device are thus enhanced.

Further scope of applicability of the present application will become more apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given herein below and the accompanying drawings which are given by way of illustration only, and thus are not limitative of the present disclosure and wherein.

DETAILED DESCRIPTION

Figure 1:
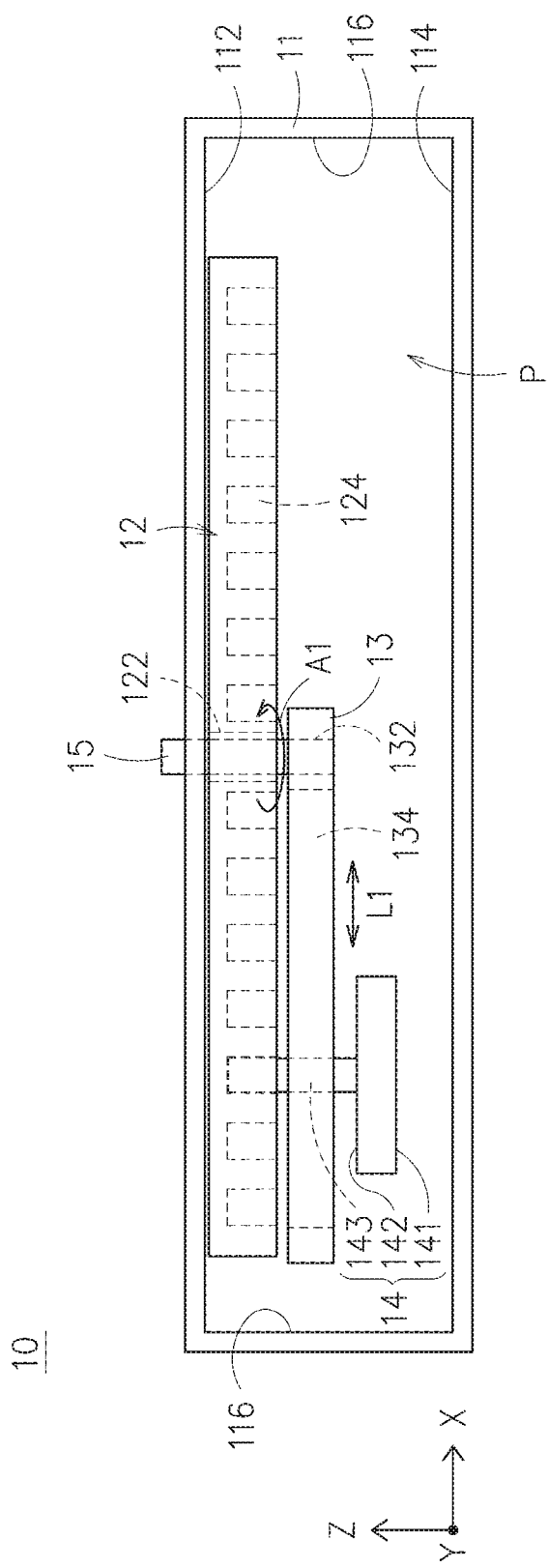
FIG. 1 is a schematic view of an embodiment of the ultrasonic probe device in accordance with this disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 2:
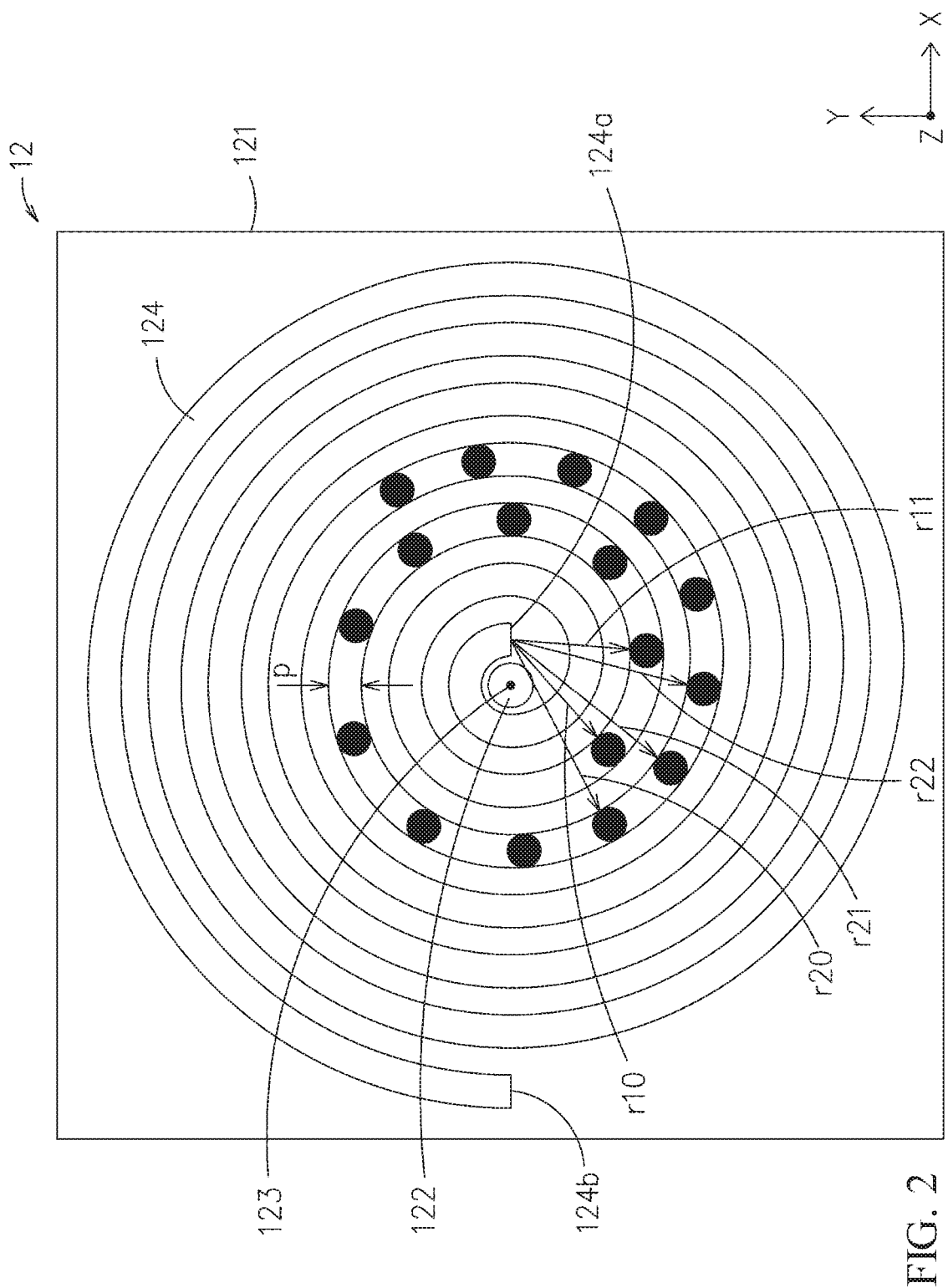
FIG. 2 is a schematic view of the spiral-track plate of FIG. 1.
Figure 3:
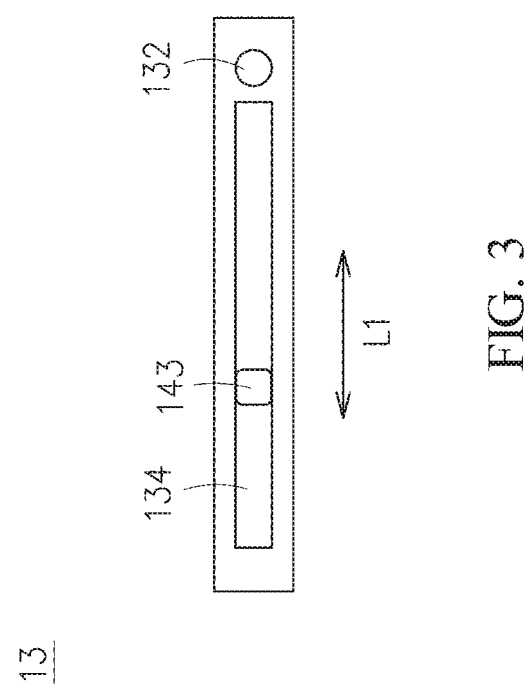
FIG. 3 is a schematic view of the driving arm of FIG. 1.

Refer to FIG. 1 through FIG. 4, FIG. 1 is a schematic view of an embodiment of the ultrasonic probe device in accordance with this disclosure. FIG. 2 is a schematic view of the spiral-track plate of FIG. 1. FIG. 3 is a schematic view of the driving arm of FIG. 1. And FIG. 4 demonstrates schematically movements of the ultrasonic probe with respect to the driving arm and the spiral-track plate of FIG. 1. As shown in FIG. 1, in this embodiment, the ultrasonic probe device 10 includes a sealed housing 11, a spiral-track plate 12, a driving arm 13, an ultrasonic probe 14 and a first shaft 15. Though the sealed housing 11 is a sealed structure, yet it can still allow the ultrasonic-wave energy generated by the ultrasonic probe 14 to penetrate therethrough. According to this disclosure, the sealed housing 11 can be an opaque structure. In some other embodiments, walls of the sealed housing 11 can be made of a transparent material or a half-transparent material.

In detail, the sealed housing 11 has a top wall 112, a bottom wall 114 and a circumferential sidewall 116, and the circumferential sidewall 116 connects between the bottom wall 114 and the top wall 112. By integrating the top wall 112, the bottom wall 114 and the circumferential sidewall 116, an accommodation room P enclosed thereinside is formed. In this disclosure, the appearance of the sealed housing 11 is not limited to any specific configuration. It shall be explained that, in the accommodation room P defined by the sealed housing of FIG. 1, the spiral-track plate 12, the driving arm 13, the ultrasonic probe 14 and part of the first shaft 15 are disposed. In particular, an upper portion of the first shaft 15 is exposed out of the top wall 112 of the sealed housing 11. For a purpose of concise explanation, FIG. 1 only illustrates those elements disposed in the accommodation room P of the sealed housing 11, such as the spiral-track plate 12, the driving arm 13, the ultrasonic probe 14 and part of the first shaft 15.

In this embodiment, the spiral-track plate 12, disposed inside the sealed housing 11, is fixed to an inner wall (in particular, the top wall 112) of the sealed housing 11. In detail, referring now also to FIG. 2, the spiral-track plate 12 includes a base plate 121, a pivotal hole 122 and a spiral groove 124. The pivotal hole 122 is located at a center 123 of the base plate 121 of the spiral-track plate 12. The spiral groove 124 is extended spirally out from the center 123 of the base plate 121 of the spiral-track plate 12. The spiral groove 124 having a predetermined depth is formed on the base plate 121 whose thickness is in a Z-axial direction. The spiral groove 124 is structured into the base plate 121 by the predetermined depth so as to form trenches, and the predetermined depth is less than the thickness of the base plate 121. In other words, the spiral groove 124 is not deep enough to penetrate through the base plate 121. As shown, the spiral groove 124 has two ends; i.e., a first end 124a and a second end 124b, in which the first end 124a is adjacent to the pivotal hole 122. The spiral groove 124 is originated from the first end 124a adjacent to the center 123 of the base plate 121 of the spiral-track plate 12, and extends outward in a spiral manner or an oval manner by encircling the center 123. Namely, a spiral radius of the spiral groove 124 with respect to the center 123 is increased gradually from the first end 124a of the spiral groove 124 to the second end 124b of the spiral groove 124. Here, the spiral radius is defined to be the distance from a position at the spiral groove 124 to the center 123.

Refer to FIG. 1 and FIG. 2. The spiral groove 124 winding in an eddy shape lies on the base plate 121 (also deem as a spiral trench in a 2D X-Y plane), and has a depth deep into the thickness of the base plate 121 (in the Z-axial direction). That is, the spiral groove 124 could be regarded as a circular spiral trench.

Figure 4:
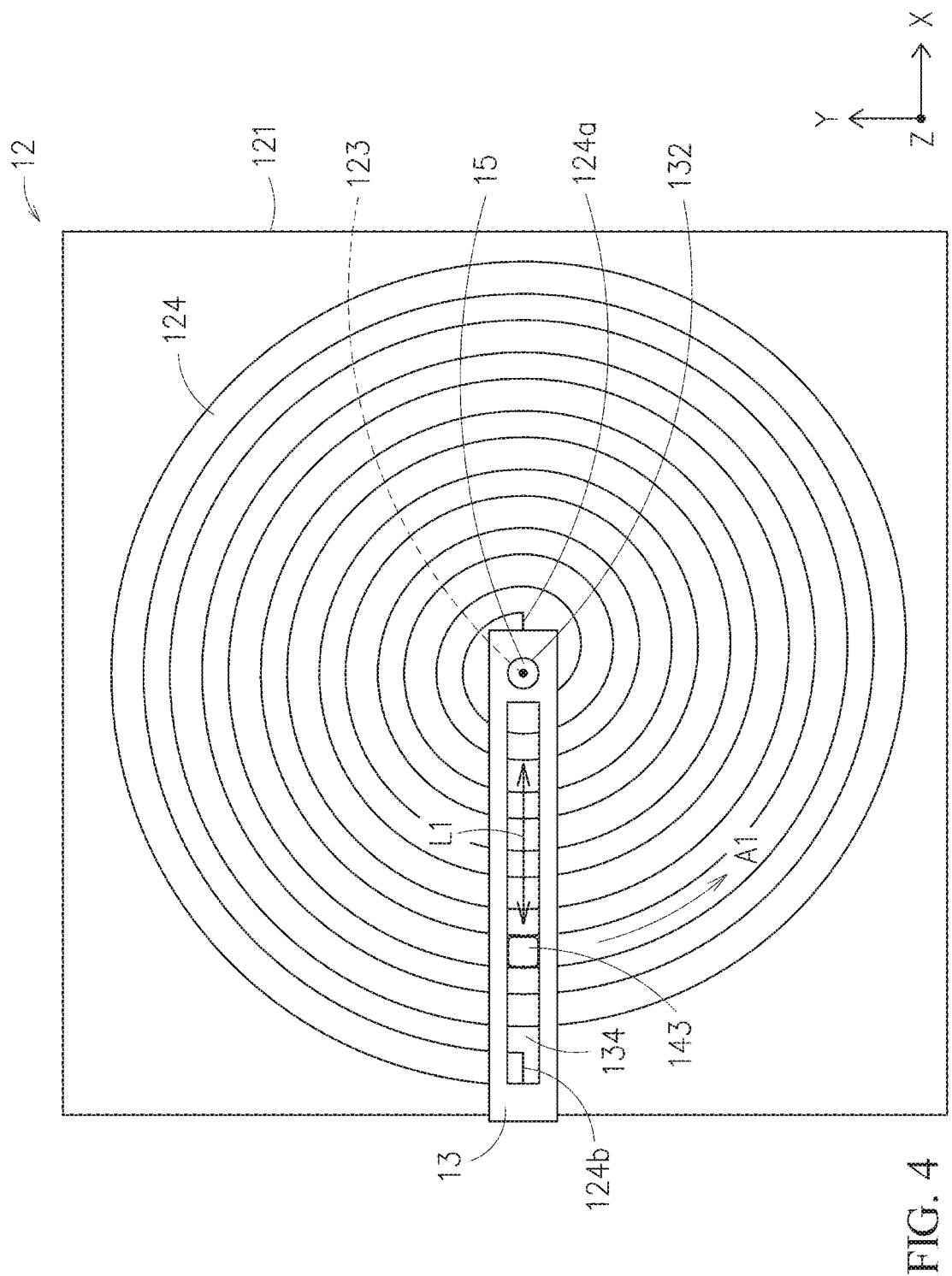
FIG. 4 demonstrates schematically movements of the ultrasonic probe with respect to the driving arm and the spiral-track plate of FIG. 1.

In this embodiment, the driving arm 13, adjacent and parallel to the spiral-track plate 12, is located under the spiral-track plate 12 in the Z-axial direction, as shown in FIG. 1. Also, the driving arm 13 is located between the spiral-track plate 12 and the ultrasonic probe 14 having a connection side 142 to face the driving arm 13. In detail, referring also to FIG. 3, the driving arm 13 includes a rotational shaft hole 132 and a first slot 134. The rotational shaft hole 132 is furnished to one end of the driving arm 13. The first slot 134 is a longitudinal hole extending lengthwise at the driving arm 13. As shown in FIG. 4, the first slot 134 shall at least have a minimal length in the X-axial direction to encompass a radial distance from the center 123 of the spiral-track plate 12 to the second end 124b of the spiral groove 124. That is, a length of the first slot 134 is at least greater than the distance from the outermost boundary of the spiral groove 124 to the center 123 of the spiral-track plate 12. The radial direction is orthogonal to an axis direction, such as the first shaft 15. As shown in FIG. 4, the center 123 also serves as the axle center of the spiral track plate 12. Therefore, the radial direction of the spiral groove 124 refers to a rectilinear direction perpendicular to the center 123 of the spiral track plate 12.

In this embodiment, as shown in FIG. 1, the rotational shaft hole 132 is located right under the pivotal hole 122. And the first shaft 15 orderly penetrates the sealed housing 11, the pivotal hole 122 of the spiral-track plate 12 and the rotational shaft hole 132 of the driving arm 13. In particular, the hole size of the pivotal hole 122 is slightly larger than the diameter of the first shaft 15, such that the spiral-track plate 12 would not be driven by the first shaft 15. Namely, the pivotal hole 122 allows the first shaft 15 to rotate freely with respect to the spiral-track plate 12. The driving arm 13 is fixed to the first shaft 15 via the rotational shaft hole 132, such that the driving arm 13 can be driven by the first shaft 15 to perform a 2D directional in-plane movement A1 for further driving the ultrasonic probe 14. In other words, as the first shaft 15 rotates in the Z-axial direction with respect to the spiral-track plate 12, the rotational shaft hole 132 associated with the first shaft 15 serves as a rotating axis for the driving arm 13. Thus, the driving arm 13 equivalently undergoes a 2D directional in-plane movement A1 with respect to the spiral-track plate 12. It shall be explained that the term "2D directional in-plane movement" is directed to a directional movement on a plane expanded by any two crossed lines or axes. For example, as shown in FIG. 1 or FIG. 4, the "2D directional in-plane movement" is the motion able to be executed on the 2D plane expanded by the X and Y axes, and this 2D plane is parallel to the base plate 121 of the spiral-track plate 12. In another embodiment, the 2D plane may be a plane expanded by the X and Z axes, or by the Y and Z axes.

In this embodiment, as shown in FIG. 1, the ultrasonic probe 14 includes a detection side 141, a connection side 142 opposing to the detection side 141, and a follower pillar 143 connecting the connection side 142. The follower pillar 143 penetrates through the first slot 134 of the driving arm 13, and then to insert into the spiral groove 124. As shown in FIG. 3, the driving arm 13 allows the follower pillar 143 to pass through the first slot 134, and also to slide along the first slot 134 to perform a 1D linear movement L1 with respect to the driving arm 13 (if the observer is located on the driving arm 13). In a further exemplary example not shown here, detection components can be individually furnished to two opposing ends of the first slot 134, so that return points of the follower pillar 143 moving along the first slot 134 can be detected. That is, as the follower pillar 143 slides along the first slot 134 and hits one of the two return points at the first end of the first slot 134, the follower pillar 143 would stop and begin to move reversely back to the second end of the first slot 134. And then, at this second end, the follower pillar 143 stops and begin to move reversely back to the first end of the first slot 134. Thereupon, in the same pattern, the follower pillar 143 can move reciprocally between the two ends of the first slot 134. Namely, the follower pillar 143 performs the 1D linear movement L1 along the first slot 134 of the driving arm 13 (if the observer is located on the driving arm 13). It shall be explained that the term "1D linear movement" is directed to a directional movement along a straight line.

In this embodiment, as shown in FIG. 1 and FIG. 4, the spiral groove 124 accommodates the free end of the follower pillar 143, and the spiral groove 124 allows the free end of the follower pillar 143 to move along the spiral groove 124. In particular, the follower pillar 143 can move from the first end 124a of the spiral groove 124 to the second end 124b of the spiral groove 124, or the follower pillar 143 can move from the second end 124b of the spiral groove 124 to the first end 124a of the spiral groove 124. Specifically, the follower pillar 143 can move along the spiral groove 124 from one arbitrary point to another arbitrary point. It shall be explained that, as the first shaft 15 rotates counter clockwisely in the Z-axial direction with respect to the spiral-track plate 12, the rotational shaft hole 132 associated with the first shaft 15 serves as a rotating axis for the driving arm 13. The driving arm 13 would rotate and perform the 2D directional in-plane movement A1 (here, a counter clockwise movement) with respect to the spiral-track plate 12. As such, the follower pillar 143 moves from the first end 124a of the spiral groove 124 to the second end 124b thereof. On the other hand, as the first shaft 15 rotates clockwisely in the Z-axial direction with respect to the spiral-track plate 12, the rotational shaft hole 132 associated with the first shaft 15 serves as a rotating axis for the driving arm 13. The driving arm 13 would rotate and perform the 2D directional in-plane movement A1 (here, a clockwise movement) with respect to the spiral-track plate 12. As such, the follower pillar 143 moves from the second end 124b of the spiral groove 124 to the first end 124a thereof. In other words, through different rotational directions of the first shaft 15, either clockwise or counter clockwise, the reciprocal movement of the follower pillar 143 between the first end 124a and the second end 124b of the spiral groove 124 can be controlled.

In an embodiment not shown here, detection components can be individually furnished to the first end 124a and the second end 124b of the spiral groove 124, respectively. Thereupon, as the follower pillar 143 moves to hit the second end 124b of the spiral groove 124, it will stop and then begin to move reversely toward the first end 124a from the second end 124b. On the other hand, as the follower pillar 143 moves to hit the first end 124a of the spiral groove 124, it will stop and then begin to move reversely toward the second end 124b from the first end 124a. Thereupon, the follower pillar 143 can move reciprocally between the first end 124a and the second end 124b of the spiral groove 124; i.e., the 2D directional in-plane movement A1 of the follower pillar 143. In practice, the ultrasonic probe 14 is to perform a planar spiral motion with respect to the spiral-track plate 12, clockwisely or counter clockwisely (if the observer is located on the spiral-track plate 12). The spiral-track plate 12 serves as a guiding member, and the driving arm 13 serves as driving and guiding members simultaneously to the ultrasonic probe 14.

Under such an arrangement, as shown in FIG. 1 and FIG. 4, the follower pillar 143 of the ultrasonic probe 14 passes through the first slot 134 and then reach into the spiral groove 124. The first shaft 15 rotates with respect to the spiral-track plate 12, and the rotational shaft hole 132 associated with the first shaft 15 serves as a rotating axis for the driving arm 13. The driving arm 13 is tightly fixed on the first shaft 15 through the rotational shaft hole 132 so that the driving arm 13 undergoes a 2D directional in-plane movement A1 with respect to the spiral-track plate 12. As the driving arm 13 is rotated, the follower pillar 143 with the free end guided by the spiral groove 124 would be driven to slide along the first slot 134, i.e., to perform the 1D linear movement L1 with respect to the driving arm 13 (if the observer is located on the driving arm 13). Thereupon, by having the first shaft 15 to rotate the driving arm 13 that allows the follower pillar 143 to slide along the first slot 134, and further by having the spiral groove 124 to guide the free end of the follower pillar 143, thus the pattern of the spiral groove 134 can be transferred to be written by the ultrasonic probe 14 through rotations of the first shaft 15. In particular, as the follower pillar 143 slides from the end of the first slot 134 adjacent to the first shaft 15 to another end of the first slot 134 away from the first shaft 15, the free end of the follower pillar 143 would trace the spiral groove 124 from the first end 124a to the second end 124b. On the other hand, as the follower pillar 143 slides from the end of the first slot 134 away from the first shaft 15 to another end of the first slot 134 adjacent to the first shaft 15, the free end of the follower pillar 143 would trace the spiral groove 124 from the second end 124b to the first end 124a. The driving arm 13 drives the follower pillar 143 to slide reciprocally between the first end 124a and the second end 124b of the spiral groove 124. When the free end of the follower arm 143 traces the spiral groove 124, the detection side 141 of the ultrasonic probe 14 moves accordingly. With the spiral groove 124 to guide the follower pillar 143 having the free end that moves along the spiral groove 124, the pattern of the spiral groove 124 would be transferred to be "written" or "printed" by the detection side 141 of the ultrasonic probe 14. In other words, the spiral groove 124 is mapped to provide a planar motion track for the detection side 141 of the ultrasonic probe 14 to perform a 2D directional in-plane movement A1 on a 2D plane expanded by the X and Y axes as shown in FIG. 4, in which the planar motion track is parallel to the spiral-track plate 12. At the same time, while the ultrasonic probe 14 moves along the planar motion track, the detection side 141 of the ultrasonic probe 14 would generate the ultrasonic-wave energy. The ultrasonic-wave energy with specific penetrability and focus ability penetrates the sealed housing 11 and to focus on an application target (for example, the subcutaneous fat layer of human body). Since the pattern of the spiral groove 124 is mapped to form the planar motion track for the detection side 141 of the ultrasonic probe 14 via the aforesaid arrangement, the ultrasonic probe 14 can perform its application task in accordance with the planar spiral track (if the observer is located on the spiral-track plate 12). Application points and distance S for each application of the ultrasonic probe 14 can be derived by the following equation.

$$S = r \times \theta \quad (1)$$

In the mathematical equation (1) listed above, S is the distance between two application points, r is the radius of the position of the application point, θ is the clockwise angle with respect to the polar axis (for 0°). It shall be explained that the term "polar axis" indicates an axis in the planar orthogonal coordinate system. In this embodiment, the negative Y axis is the polar axis. In another embodiment, the positive X axis can be the polar axis. By referring to FIG. 2, given the first end 124a of the spiral groove 124 as the polar point, the radius grows gradually bigger from the first end 124a outward to the second end 124b of the spiral groove 124; i.e., in an ascendant manner along the spiral groove 124. For example, as shown in FIG. 2, a 2 mm is set to separate every two consecutive application points of the ultrasonic probe 14, r10 stands for the radius of the application point at the first circular track (i.e., the distance from the polar point to the application point). For a r10=5 mm, then θ=22.9° (noted that the polar axis is the negative Y axis, and the angle is measured clockwisely from the polar axis). For another example, r20 stands for the radius of the application point at the second circular track. For a r20=7 mm, then θ=16.4°. In other words, through the radius and angle in the polar coordinate system, the application points of the ultrasonic probe 14 in each circular track can be clearly defined. Further, in the same circular track, different positions of the ultrasonic probe 14 can be realized by Equation (2) as follows.

$$r2 = r1 + (p/360) \times \theta \quad (2)$$

In Equation (2), r2 is the radius of the application point, r1 is the radius of a previous application point before the aforesaid application point with r2, and p is the pitch distance of the two neighboring circular tracks (measured a track center to another neighboring track center). For example, as shown in FIG. 2, in the first circular track, r11 is the radius of the application point, and r10 is the radius of a previous application point before the aforesaid application point with r11, in which the r10 is given. From Equation (2), the r11 can be obtained. Further, through Equation (1), the angle θ of the application point can be obtained. Similarly, in the second circular track, r21 (radius of the point to be applied) can be used to derive r22 (radius of the next application point). Thus, through the radius and angle in the polar coordinate system, the application points of the ultrasonic probe 14 can be clearly controlled. In addition, it shall be explained that each block node of FIG. 2 stands for one application point of the ultrasonic probe 14, and each block node actually is mapped from one corresponding position at the spiral groove 124 via the follower pillar 143.

As described above, when the follower pillar 143 moves along the spiral groove 124, the ultrasonic probe 14 having the detection side 141 moves synchronously. According to positions of application points and pitches, the detection side 141 of the ultrasonic probe 14 would apply ultrasonic-wave energy onto the application target (for example, the subcutaneous fat layer of human body) within a planar block. Thus, the operator needn't to move the ultrasonic probe device 10 by hands, and the application target (for example, the subcutaneous fat layer of human body) within a planar block having hundreds or thousands of points to be treated by the ultrasonic-wave energy. Since the distance between the ultrasonic probe device 10 and the application target (for example, the subcutaneous fat layer of human body) is fixed, the application depth of the ultrasonic-wave energy within the planar block can be kept uniformly.

Further, the ultrasonic probe device 10 of this embodiment is to arrange the ultrasonic probe 14, the spiral-track plate 12 and the driving arm 13 inside the sealed housing 11. By having the follower pillar 143 of the ultrasonic probe 14 to penetrate through the first slot 134 and to further engage the spiral groove 124, the ultrasonic probe 14 can then apply ultrasonic-wave energy within the planar block with a certain depth.

In addition, the ultrasonic probe device of this disclosure can be arbitrarily replaced or assembled by related ultrasonic components so as to execute a specific planar block, and the associated replace ability and convenience of the device are thus enhanced.

Figure 5:
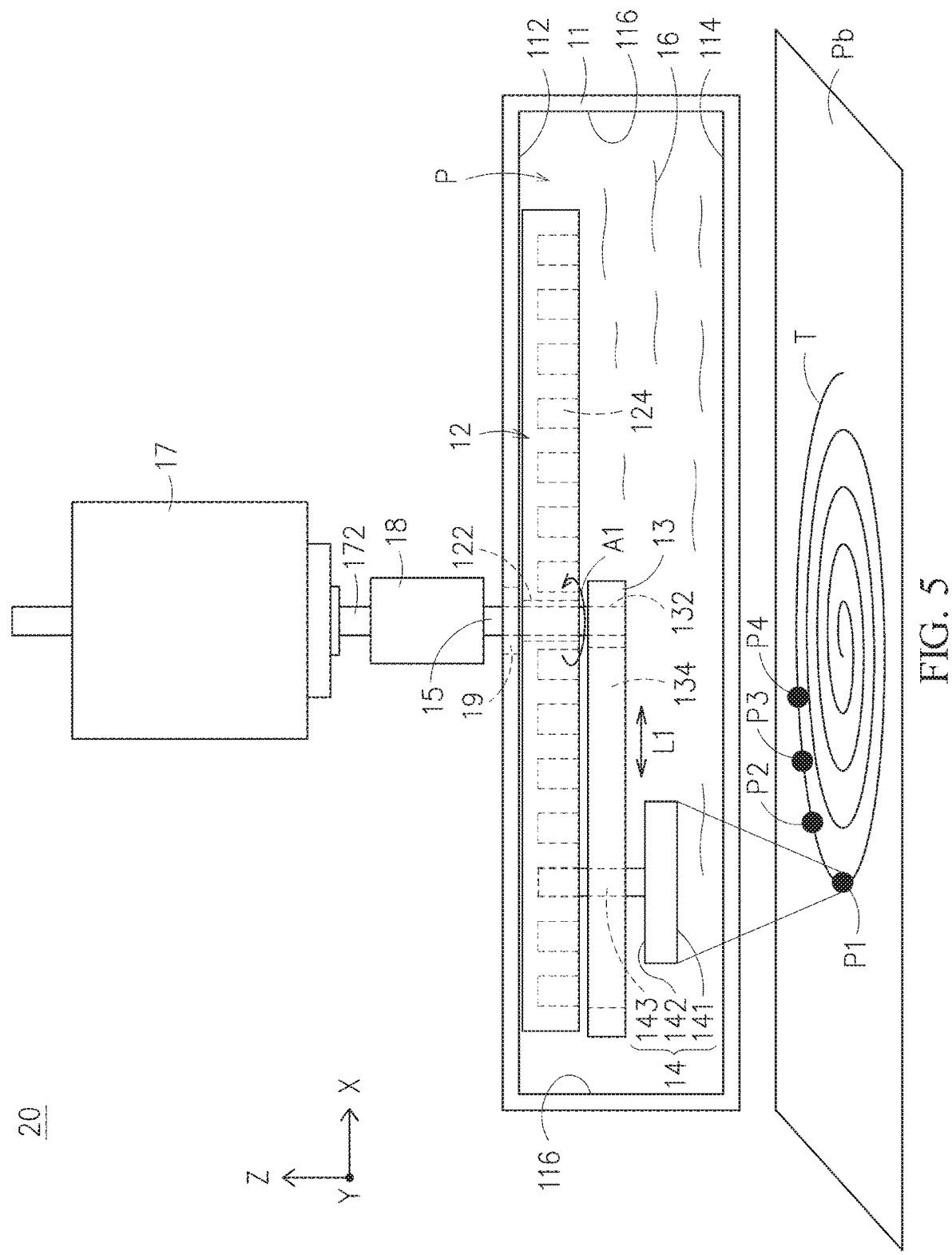
FIG. 5 is a schematic view of another embodiment of the ultrasonic probe device in accordance with this disclosure.

Referring now to FIG. 5, a schematic view of another embodiment of the ultrasonic probe device in accordance with this disclosure is shown. It shall be explained that the ultrasonic probe device 20 of FIG. 5 and the ultrasonic probe device 10 of FIG. 1 are similar. Thus, the elements with the same functions are assigned by the same numbers, and details thereabout are omitted herein. The major difference between the ultrasonic probe device 20 of FIG. 5 and the ultrasonic probe device 10 of FIG. 1 is that, in this embodiment, the ultrasonic probe device 20 further includes a liquid medium 16, a motor 17, a shaft coupler 18 and a sealing element 19. In addition, for a concise description, a planar block PB of an application target (for example, the subcutaneous fat layer of human body) is schematically plotted under the ultrasonic probe device 20.

In this embodiment, the liquid medium 16 is filled into the accommodation room P of the sealed housing 11 so as to completely soak thereinside the ultrasonic probe 14, the spiral-track plate 12 and the driving arm 13. The liquid medium 16 can promote the transmission of the ultrasonic-wave energy so as to enhance the transmission efficiency of the ultrasonic-wave energy onto the application target (for example, the subcutaneous fat layer of human body) and to reduce the loss of the ultrasonic-wave energy. It shall be explained that the type of the liquid medium in this disclosure is not specifically limited. For example, the water or the like liquid medium can be used as the liquid medium for transmitting the ultrasonic-wave energy. As described above, the follower pillar 143 moves along the spiral groove 124 so as to drive synchronously the detection side 141 of the ultrasonic probe 14. At the meantime, the detection side 141 of the ultrasonic probe 14 would issue corresponding ultrasonic-wave energy onto the planar block PB of the application target (for example, the subcutaneous fat layer of human body) according to positions of the predetermined application points and pitches. Since the spiral groove 124 provides a planar motion track T for the detection side 141 of the ultrasonic probe 14 to follow, the operator can apply ultrasonic-wave energy onto hundreds or thousands of application points within the planar block PB of the application target (for example, the subcutaneous fat layer of human body) without moving the ultrasonic probe device 20. For example, as shown in FIG. 5, at least four separate focal points P1~P4 (i.e., application points) are located at the planar motion track T. Since the distance between the ultrasonic probe device 20 and the application target (for example, the subcutaneous fat layer of human body) is fixed, the application depths at individual focal points P1~P4 issued by the ultrasonic probe 14 can be substantially kept the same. Thereupon, better uniformity of the application depth of the applied ultrasonic-wave energy over the planar block PB (including focal points P1~P4) can be obtained.

In addition, this embodiment further provides a sealing element 19. While the first shaft 15 penetrates the top wall 112 of the sealed housing 11, the sealing element 19 is furnished between the first shaft 15 and the top wall 112 of the sealed housing 11. As such, the tightness of the sealed housing 11 can be ensured, and possible leakage of the liquid medium 16 can be avoided. In one embodiment, the sealing element 19 can be, but not limited to, an O-ring.

In this embodiment, the motor 17 includes a second shaft 172 and a shaft coupler 18 coupled with one end of the second shaft 172. The shaft coupler 18 is introduced to engage the second shaft 172 and the first shaft 15. In particular, the first shaft 15 can be different to the second shaft 172. Under such an arrangement, the spiral groove 124 is used to provide the planar motion track for the detection side 141 of the ultrasonic probe 14 to follow, and the motor 17 and the driving arm 13 move the ultrasonic probe 14. The motor 17 rotates the second shaft 172, then the first shaft 15 is rotated by the second shaft 172 through the shaft coupler 18. Then the first shaft 15 swings the driving arm 13, and finally the follower pillar 143 sliding along the first slot 134 of the driving arm 13 and being regulated by the spiral groove 124 is to have the ultrasonic probe 14 to follow the planar motion track to further apply the ultrasonic-wave energy. Thus, in this embodiment, a single driving element (i.e., the motor 17) is used to achieve the goal of applying the ultrasonic-wave energy from the ultrasonic probe 14 to work on the predetermined planar block PB.

Figure 6:
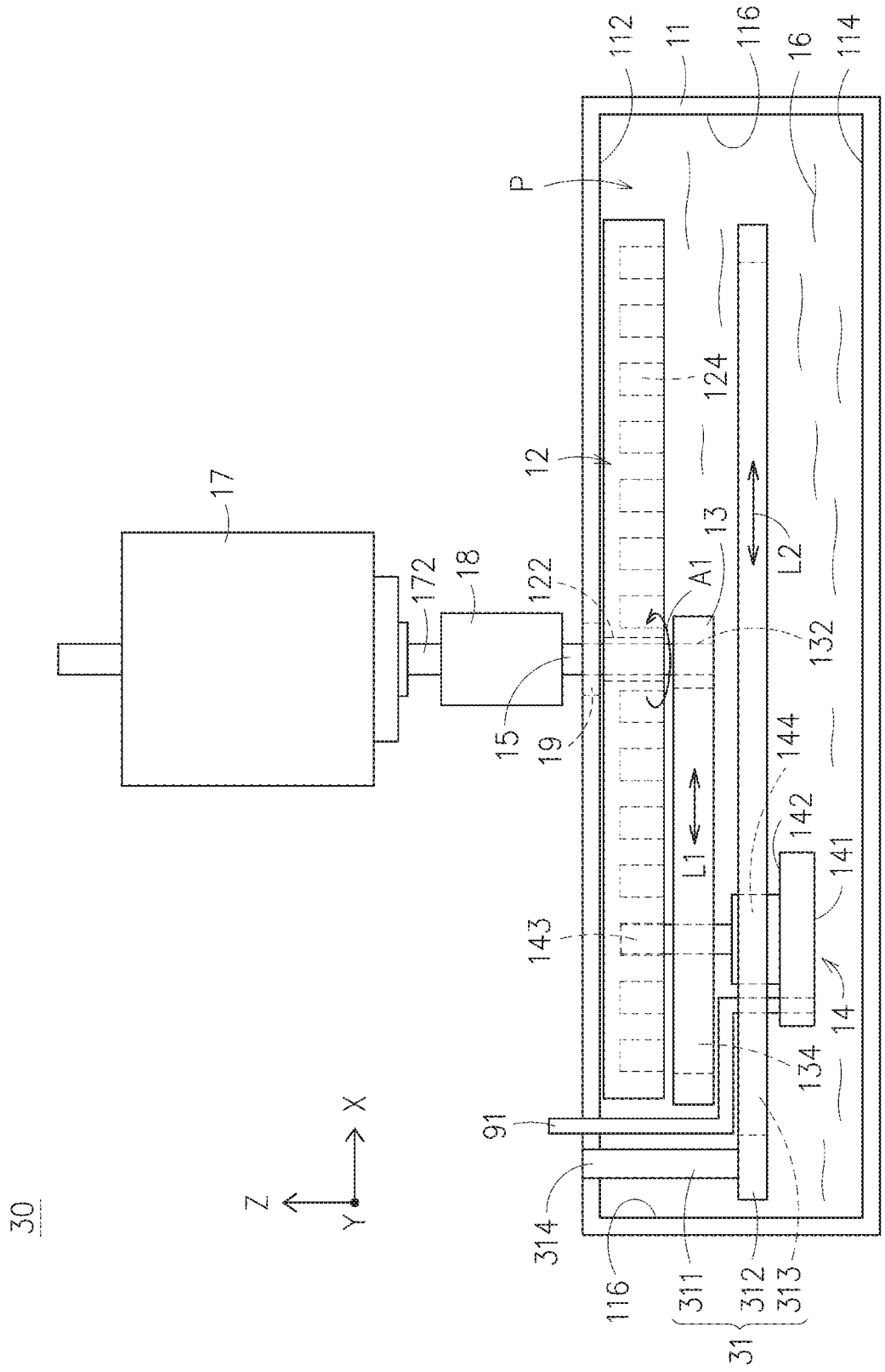
FIG. 6 is a schematic view of a further embodiment of the ultrasonic probe device in accordance with this disclosure.
Figure 7:
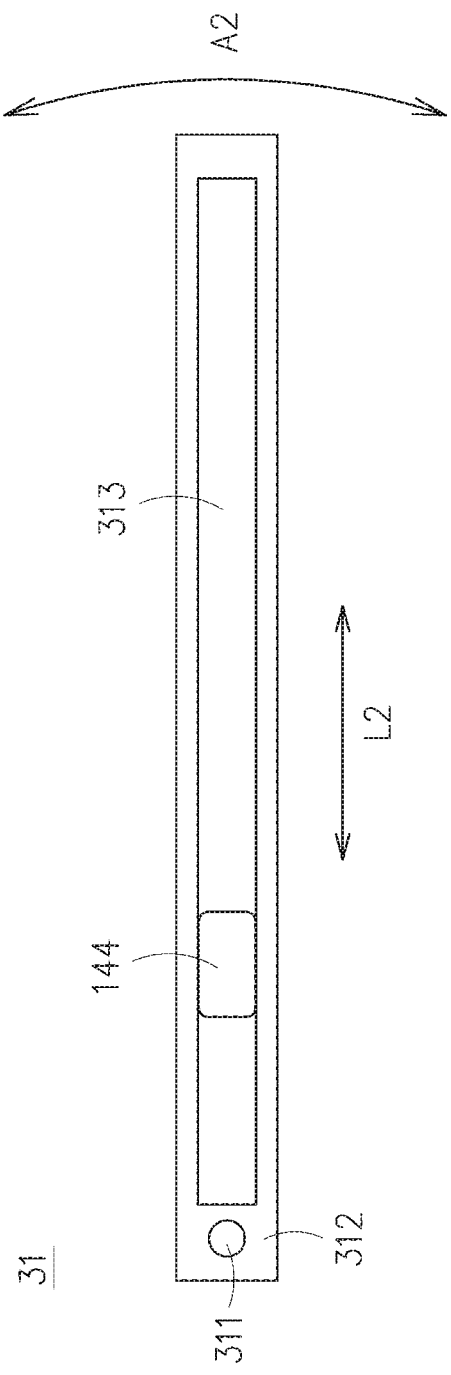
FIG. 7 is a schematic view of the L-shape guide member of FIG. 6.
Figure 8:
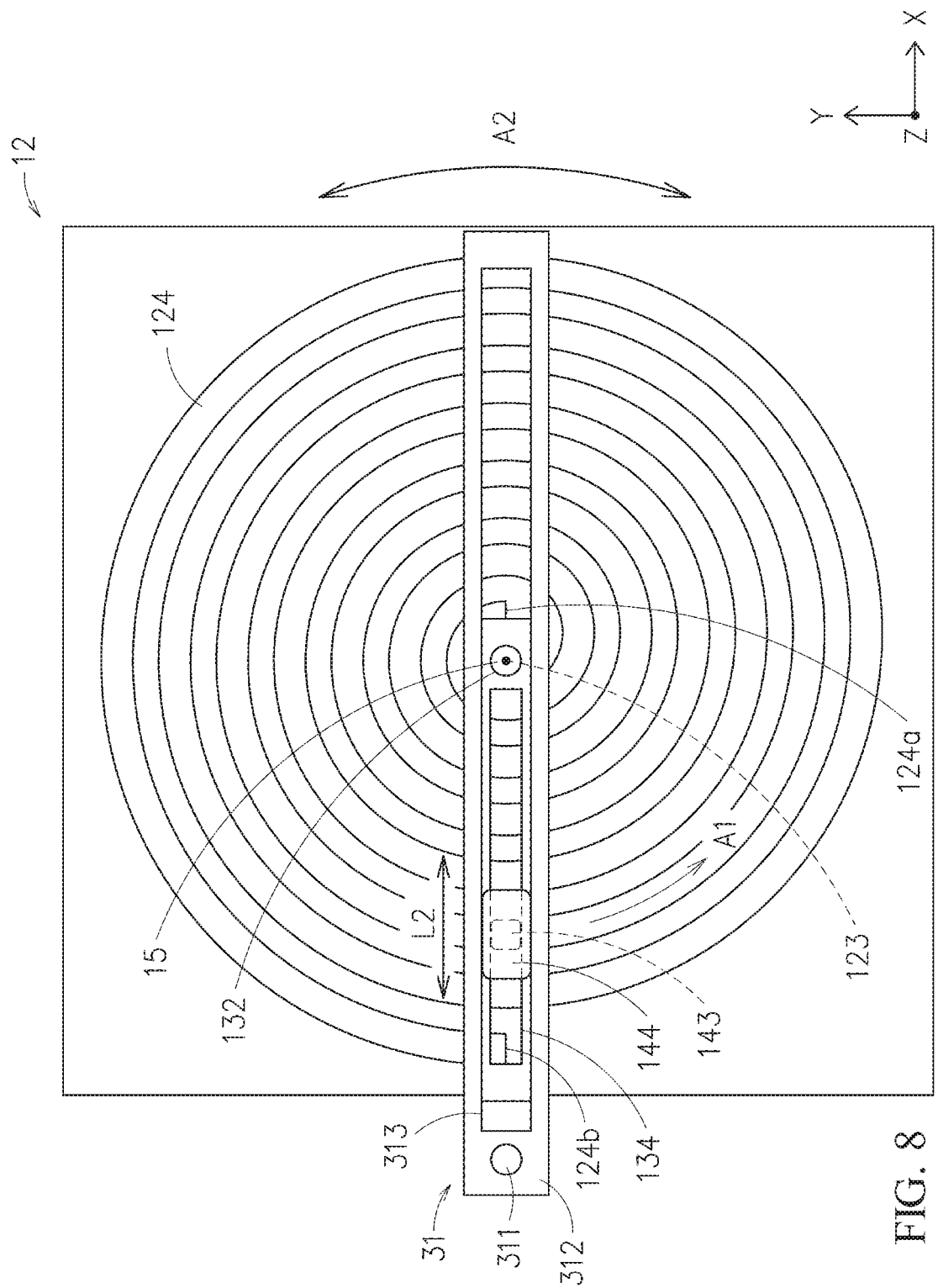
FIG. 8 demonstrates schematically movements of the ultrasonic probe with respect to the driving arm and the spiral-track plate of FIG. 6.

Refer now to FIG. 6 through FIG. 8. FIG. 6 is a schematic view of a further embodiment of the ultrasonic probe device in accordance with this disclosure. FIG. 7 is a schematic view of the L-shape guide member 31 of FIG. 6. FIG. 8 demonstrates schematically movements of the ultrasonic probe 14 with respect to the driving arm 13 and the spiral-track plate 12 of FIG. 6. It shall be explained that the ultrasonic probe device 30 of FIG. 6 and the ultrasonic probe devices 10, 20 of FIGS. 1, 5, respectively, are largely similar Thus, the elements with the same functions are assigned by the same numbers, and details thereabout are omitted herein. The major difference between the ultrasonic probe device 30 of FIG. 6 and the ultrasonic probe device 20 of FIG. 5 is that, in this embodiment, the ultrasonic probe device 30 further includes an L-shape guide member 31 and at least two cables 91 (positive and negative terminals). The L-shape guide member 31 for guiding the cables 91 is to prevent the cables 91 from being messed up, while the ultrasonic probe 14 performs the planar spiral motion. With respect to the spiral-track plate 12, the L-shape guide member 31 can only swing left and right within a small angular range (less than 180°) in an arc direction A2 (noted that the previous 2D directional in-plane movement A1 for the driving arm 13 is a full 360° range). Since the follower 144 is limited within the second slot 313 to undergo a 1D linear movement L2 with respect to the L-shape guide member 31 (if the observer is located on the L-shape guide member 31), the cables 91 can ride the follower 144 to extend or shrink in the second slot 313. And thus possible twist or rotations thereupon can be substantially reduced. Hence, by having the cables 91 to co-move with the L-shape guide member 31, then improper cable twist or bent can be substantially reduced.

In this embodiment, as shown in FIG. 6, the L-shape guide member 31 includes a short-leg portion 311 and a guide portion 312. One end of the short-leg portion 311 has a pivotal shaft 314 to be mounted onto the sealed housing 11. As shown in FIG. 6, the spiral-track plate 12 and the pivotal shaft 314 of the short-leg portion 311 are fixed to an inner wall (top wall 112 for example) of the sealed housing 11, by having the spiral-track plate 12 adjacent to the pivotal shaft 314 of the short-leg portion 311. In addition, the cables 91 are connected to the detection side 141 of the ultrasonic probe 14, and the cable 91 extends along the short-leg portion 311. As shown in FIG. 6, the pivotal shaft 314 of the short-leg portion 311 is located exteriorly to the spiral-track plate 12. A portion of the cables 91 is located between the short-leg portion 311 and the spiral-track plate 12, and another portion of the cables 91 is located between the short-leg portion 311 and the driving arm 13. And rest of the cables 91 are extended under the driving arm 13 and further connect to the detection side 141 of the ultrasonic probe 14.

As shown in FIG. 6, another end of the short-leg portion 311 is connected with the guide portion 312, in which the guide portion 312 is located between the driving arm 13 and the connection side 142 of the ultrasonic probe 14. In other words, the short-leg portion 311 extending in the Z-axial direction has a length at least greater than a sum of thicknesses of the spiral-track plate 12 and the driving arm 13 in the Z-axial direction. As such, the guide portion 312 can be located under the spiral-track plate 12 and the driving arm 13.

In this embodiment, as shown in FIG. 7 and FIG. 8, the guide portion 312 has a second slot 313 formed as a longitudinal hole extending along almost the entire guide portion 312. The second slot 313 for allowing a 1D linear movement L2 (in the X-axial direction) therealong has a width different to that of the first slot 134. The width of the second slot 313 is greater than that of the first slot 134. As shown in FIG. 6 and FIG. 8, a length of the guide portion 312 (in the X-axial direction) is at least greater than that of either the spiral-track plate 12 or the driving arm 13. Namely, the length of the second slot 313 in the X-axial direction covers at least any two outmost rims of the spiral groove 124; for example, a distance between the second end 124b to the farthest end of the spiral groove 124 on the extension line connecting the first end 124a and the second end 124b, as shown in FIG. 8.

In this embodiment, as shown in FIG. 6 and FIG. 8, the ultrasonic probe 14 includes a follower 144 located between the follower pillar 143 and the connection side 142. The follower 144 can be shaped into a cube form or a cuboid form. The follower 144 is longer than that of the follower pillar 143 in the X-axial direction. The second slot 313 extended for allowing the 1D linear movement L2 in the X-axial direction contains and guides the follower 144 to undergo the 1D linear movement L2 (if the observer is located on the L-shape guide member 31).

Under such an arrangement, as shown in FIG. 6, the follower pillar 143 of the ultrasonic probe 14 penetrates through the first slot 134 and engages in the spiral groove 124. As the first shaft 15 rotates, the spiral-track plate 12 is stationary, and the rotational shaft hole 132 associated with the first shaft 15 serves as a rotating axis for the driving arm 13. With respect to the spiral-track plate 12, the driving arm 13 performs the 2D directional in-plane movement A1 to drive and slide the follower pillar 143 to be guided by the spiral groove 124. In other words, as the follower pillar 143 undergoes the 1D linear movement L1 along the first slot 134 (if the observer is located on the driving arm 13), the follower pillar 143 is restrained by the spiral groove 124 to move reciprocally between the first end 124a and the second end 124b of the spiral groove 124. In addition, as shown in FIG. 8, while the movement of the follower pillar 143 is guided by the spiral groove 124, the detection side 141 of the ultrasonic probe 14 would move only along a planar motion track. The follower pillar 143 is co-moved with the follower 144. The guide portion 312 has the pivotal shaft 314 as the rotational shaft to swing over the spiral-track plate 12. In other words with respect to the spiral-track plate 12, the driving arm 13 is to undergo a 2D directional in-plane movement A1 over the spiral-track plate 12 for a 360° range. Since the follower 144 is limited by the second slot 313 to undergo only the 1D linear movement L2 (if the observer is located on the L-shape guide member 31), and also no rotation of the follower 144 in the second slot 313 is allowed. Thereupon, the guide portion 312 can undergo the swinging within a predetermined angular range in the arc direction A2 with respect to the spiral-track plate 12. Thus, as the guide portion 312 co-moves the cables 91, possible twisting or bending upon the cables 91 can be reduced to some degree. As shown in FIG. 8, the guide portion 312 can swing within a predetermined angular range with respect to the spiral-track plate 12, and the corresponding arc direction A2 is parallel to the 2D directional in-plane movement A1. Therefore, the spiral groove 124, the first slot 134 and the second slot 313 are cooperated to provide a planar motion track for the detection side 141 of the ultrasonic probe 14 to follow. While the motor 17 drives the driving arm 13 as well as the ultrasonic probe 14, the ultrasonic probe 14 can be applied in accordance with the planar spiral track (if the observer is located on the spiral-track plate 12).

Figure 9:
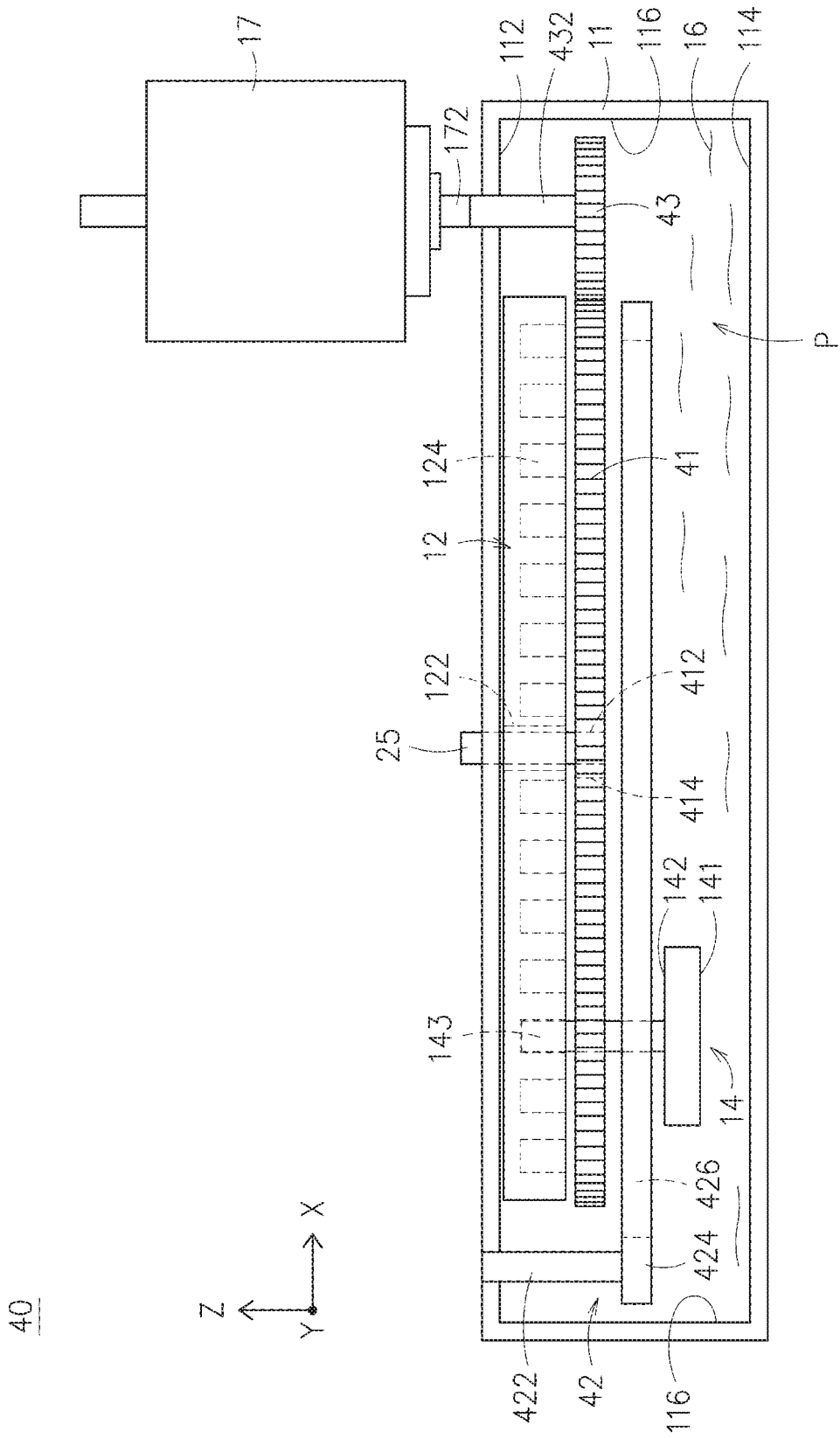
FIG. 9 is a schematic view of one more embodiment of the ultrasonic probe device in accordance with this disclosure.
Figure 10:
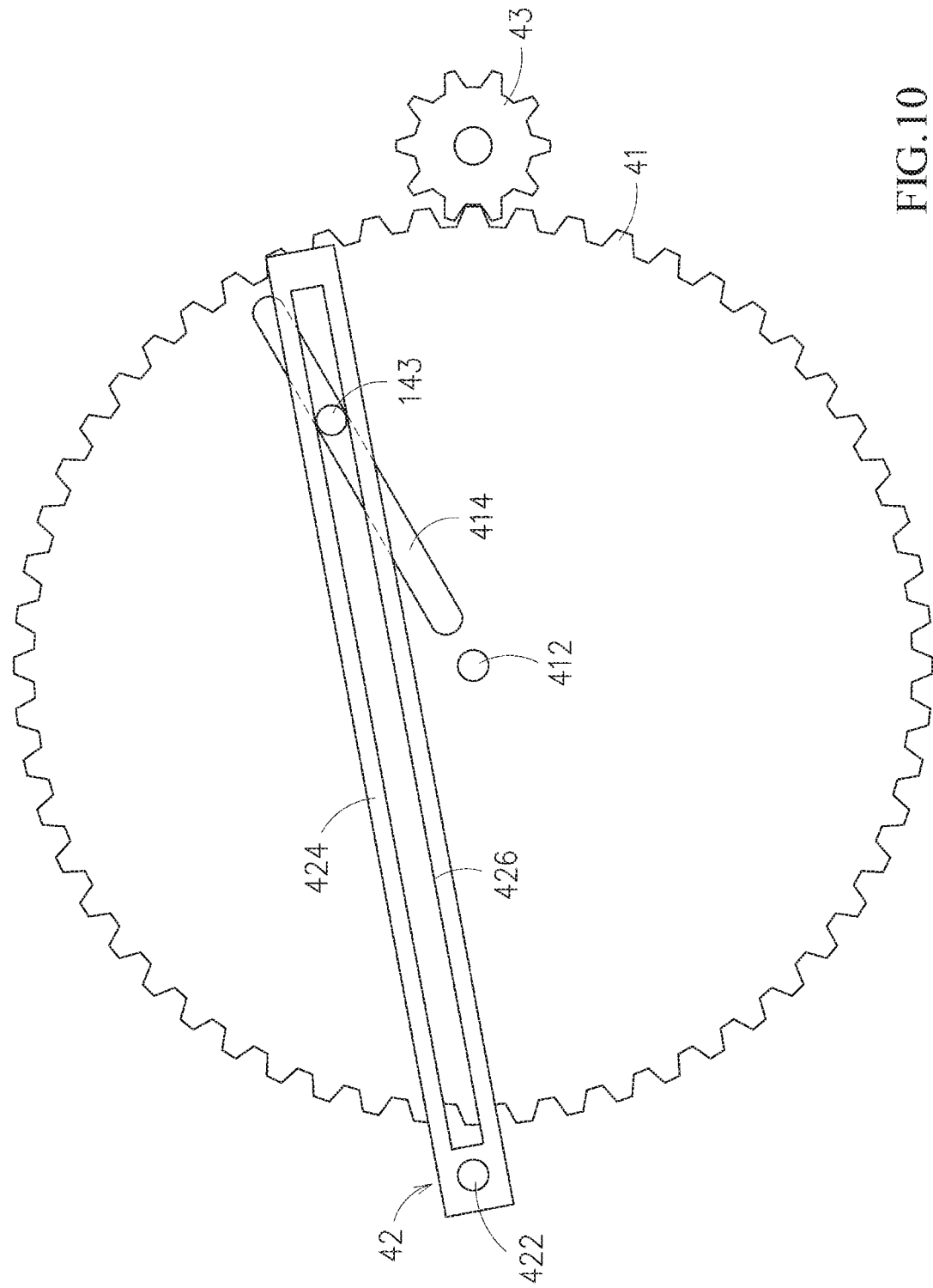
FIG. 10 demonstrates schematically an arrangement of the gear, the rocker arm and the pinion of FIG. 9.

Refer now to FIG. 9 through FIG. 10; where FIG. 9 is a schematic view of one more embodiment of the ultrasonic probe device 40 in accordance with this disclosure. FIG. 10 demonstrates schematically an arrangement of a gear 41, a rocker arm 42 and a pinion 43 of FIG. 9. It shall be explained that the ultrasonic probe device 40 of FIG. 9 and the ultrasonic probe devices 10, 20, 30 of FIGS. 1, 5, 6 respectively, are largely similar. Thus, the elements with the same functions are assigned by the same numbers, and details thereabout are omitted herein. The major difference between the ultrasonic probe device 40 of FIG. 9 and the ultrasonic probe device 20 of FIG. 5 is that, in this embodiment, the ultrasonic probe device 40 further includes a gear 41, a rocker arm 42, a pinion 43 and a shaft 25. Simply speaking, the gear 41, to replace the driving arm 13 of FIG. 1, FIG. 5 or FIG. 6, is to drive and guide the ultrasonic probe 14.

In this embodiment, the gear 41, located inside the accommodation room P of the sealed housing 11, is adjacent to the spiral-track plate 12. As shown in FIG. 9, in the Z-axial direction, the gear 41, under the spiral-track plate 12, is located between the spiral-track plate 12 and the connection side 142 of the ultrasonic probe 14. In addition, the length of the gear 41 (i.e., the diameter thereof in the X-axial direction) shall at least cover a distance of any two outermost points of the spiral groove 124.

In this embodiment, as shown in FIG. 10, the gear 41 has a center pivotal hole 412 and a first slot 414, in which the center pivotal hole 412 is located at the center of the gear 41. The first slot 414, adjacent to the center pivotal hole 412, lies in a radial direction of the gear 41 outward from the center pivotal hole 412. The first slot 414 can be a longitudinal hole penetrating through the gear 41, and the first slot 414 of the gear 41 is to contain the follower pillar 143 and limit the follower pillar 143 only to undergo a 1D linear movement (if the observer is located on the gear 41). As shown in FIG. 10, the center pivotal hole 412 of the gear 41 is aligned with the pivotal hole 122 of the spiral-track plate 12, and the shaft 25 penetrates through both the pivotal hole 122 and the center pivotal hole 412. The shaft 25 has an axis direction, and the radial direction of the gear 41 is orthogonal to the axis direction of the center pivotal hole 412.

In this embodiment, as shown in FIG. 9, the pivotal hole 122 is located at the center of the spiral-track plate 12. The center pivotal hole 412 is aligned with the pivotal hole 122, and the shaft 25 is orderly to penetrate through the sealed housing 11, the pivotal hole 122 of the spiral-track plate 12, and the center pivotal hole 412 of the gear 41. In this embodiment, the diameter of the pivotal hole 122 is slightly greater than the diameter of the shaft 25, such that the spiral-track plate 12 can be stationary with respect to rotation of a rotating shaft 25. In other words, the pivotal hole 122 allows the shaft 25 to rotate with respect to the spiral-track plate 12. The gear 41 is fixed to the shaft 25 via the center pivotal hole 412, so that the gear 41 can co-move the shaft 25. In other words, the shaft 25 engaging the center pivotal hole 412 serves as a rotating axis for the gear 41. The shaft 25 has an axis direction equivalent to the Z-axial direction and rotates with respect to the spiral-track plate 12.

In this embodiment, as shown in FIG. 9, the gear 41 is located between the spiral-track plate 12 and the rocker arm 42, and one end of the rocker arm 42 has a pivotal shaft 422 to be fixed to the sealed housing 11. As shown in FIG. 9, both the spiral-track plate 12 and the pivotal shaft 422 of the rocker arm 42 are individually fixed to an inner wall (the top wall 112 for example) of the sealed housing 11, and the spiral-track plate 12 is adjacent to the pivot shaft 422 of the rocker arm 42. In addition, as shown in FIG. 10, the rocker arm 42 has an arm portion 424 and a second slot 426. The arm portion 424 connects to the pivotal shaft 422, which is located outside of the spiral-track plate 12. The pivotal shaft 422 serves as a rotating axis for the arm portion 424 of the rocker arm 42, and the arm portion 424 swings with respect to the spiral-track plate 12. In this embodiment, the rocker arm 42 is to guide the cable (not shown in the figure) so as to prevent the cable from being improper twisted or bent upon when the ultrasonic probe 14 undergoes a planar spiral motion. The second slot 426 is formed as a longitudinal hole extending lengthy along the arm portion 424. In other words, a length of the second slot 426 is extended to allow the 1D linear movement. The length of the second slot 426 is different to that of the first slot 414. As shown in FIG. 9 or FIG. 10, the second slot 426 is longer than the first slot 414, and the second slot 426 is wider than the first slot 414.

Under such an arrangement, as shown in FIG. 9, the follower pillar 143 of the ultrasonic probe 14 penetrates through the second slot 426 and the first slot 414, and finally enters the spiral groove 124. The shaft 25 is rotated with respect to the spiral-track plate 12. At the meantime, the shaft 25 engaging the center pivotal hole 412 serves as a rotating axis for the gear 41. Thus, the follower pillar 143 is guided to slide along the spiral groove 124. As shown in FIG. 10, the follower pillar 143 performs the 1D linear movement along the first slot 414 (if the observer is located on the gear 41). At the meantime, the follower pillar 143 also undergo another 1D linear movement along the second slot 426 (if the observer is located on the rocker arm 42). Then, the follower pillar 143 can proceed a reciprocal motion along the spiral groove 124 (if the observer is located on the spiral-track plate 12). As a whole, the follower pillar 143 moves along the planar spiral track (if the observer is located on the spiral-track plate 12). In addition, as the follower pillar 143 moves along the spiral groove 124, the detection side 141 of the ultrasonic probe 14 can follow the planar spiral track to move (if the observer is located on the spiral-track plate 12). The planar motion track is defined as the 2D directional in-plane movement of the ultrasonic probe 14, which is parallel to the spiral-track plate 12. The 2D directional in-plane is constituted by any two axis, such as the X axis and the Y axis.

In addition, as shown in FIG. 9, the pinion 43 is adjacent to the gear 41, and modules of the pinion 43 are less than these of the gear 41. The pinion 43 meshing the gear 41 includes a first shaft 432 connecting a second shaft 172 of a motor 17. As the motor 17 rotates the second shaft 172, the motor power is then transmitted to the first shaft 432. Then, the first shaft 432 would rotate the pinion 43 as well as the gear 41 that meshes the pinion 43. Thereby, the gear 41 would rotate with respect to the spiral-track plate 12. Such that, as described above, the ultrasonic probe 14 would undergo a planar spiral track to apply the ultrasonic-wave energy. Thus, the object of this disclosure to provide the ultrasonic probe 14 that can apply the ultrasonic-wave energy within the planar block simply by a single driving element (the motor 17 for example) can be achieved. In addition, the motor 17 for driving the pinion 43 can rotate clockwisely or counter clockwisely to control the reciprocal motion of the follower pillar 143 along the spiral groove 124.

In summary, in the ultrasonic probe device of this disclosure, the ultrasonic probe moves along the planar motion track inside the sealed housing. Since the spiral groove provides the planar motion track for the detection side of the ultrasonic probe to follow, the ultrasonic probe can follow the planar spiral track to apply the ultrasonic-wave energy. In addition, since the operator can apply ultrasonic-wave energy onto hundreds or thousands of application points within the planar block of the application target (for example, the subcutaneous fat layer of human body) without moving the ultrasonic probe device. Since the distance between the ultrasonic probe device and the application target (for example, the subcutaneous fat layer of human body) is fixed, better uniformity of the application depth of the applied ultrasonic-wave energy over the planar block can be obtained.

Further, by disposing the ultrasonic probe, the spiral-track plate and the driving arm inside the sealed housing of the ultrasonic probe device provided in accordance with this disclosure, and further through kinematic relationships established by having the follower pillar to penetrate through slots (the first slot for example) and engaging the spiral groove, the ultrasonic probe can apply ultrasonic-wave energy within the planar block.

In addition, the ultrasonic probe device of this disclosure can be arbitrarily replaced or assembled by related ultrasonic components so as to execute a specific planar block, and the associated replace ability and convenience of the device are thus enhanced.

In addition, in this disclosure, the liquid medium is filled into the sealed housing for promoting the transmission of the ultrasonic-wave energy. As such, the transmission efficiency of the ultrasonic-wave energy onto the application target (for example, the subcutaneous fat layer of human body) is enhanced and the loss of the ultrasonic-wave energy is reduced.

In addition, in comparison with the prior art to use two motors for controlling respective curve-surface motions, this disclosure can utilize only one single driving element (the motor) to have the ultrasonic probe to apply ultrasonic-wave energy within the planar block.

Further, the ultrasonic probe device provided by this disclosure introduces an L-shape guide member and a square follower. Since the square follower is not rotational within the second slot, a guide portion of the L-shape guide member can only swing within an angular range with respect to the spiral-track plate. Such that possible twisting and bending of the cable can be reduced upon when the guide portion and the cable are moved simultaneously.

Furthermore, the ultrasonic probe device provided by this disclosure introduces a gear and a rocker arm. Through the kinematic relationships established by having the follower pillar to penetrate through slots (the first and second slots for example) and engaging the spiral groove, the ultrasonic probe can apply ultrasonic-wave energy within the planar block. In addition, in this embodiment, a pinion as a power transmission component can be introduced to mesh the gear.

With respect to the above description then, it is to be realized that the optimum dimensional relationships for the parts of the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

What is claimed is:

1. An ultrasonic probe device, comprising:
a sealed housing;
a spiral-track plate, disposed inside the sealed housing, comprising a pivotal hole and a spiral groove, the spiral groove being extended outward from a center of the spiral-track plate;
an arm, comprising an arm slot and an arm hole;
an ultrasonic probe, comprising a follower, a follower pillar, a detection side and a connection side opposing to the detection side, wherein the follower pillar of the ultrasonic probe connects to the connection side via penetrating through the arm slot in the arm and entering the spiral groove, and the spiral groove provides a planar motion track to the detection side of the ultrasonic probe;
a center shaft, penetrating through the sealed housing and the pivotal hole of the spiral-track plate; and
an L-shape guide member, wherein the L-shape guide member comprises a leg portion and a guide portion having a guide slot, with one end of the leg portion, which serves as a pivotal shaft, affixed to the sealed housing, and another end of the leg portion connected to the guide portion;
wherein the follower of the ultrasonic probe attaches to the connection side by penetrating through the guide slot in the guide portion.

2. The ultrasonic probe device of claim 1, wherein the arm is located between the spiral-track plate and the connection side of the ultrasonic probe.

3. The ultrasonic probe device of claim 1, wherein the pivotal hole is located at the center of the spiral-track plate, the pivotal hole allowing the center shaft to rotate with respect to the spiral-track plate.

4. The ultrasonic probe device of claim 1, wherein the arm hole is located at one end of the arm, the arm slot is adjacent to the arm hole, and the arm is fixed with the center shaft via the arm hole.

5. The ultrasonic probe device of claim 1, wherein the planar motion track defines 2D directional in-plane movements of the ultrasonic probe parallel to the spiral-track plate.

6. The ultrasonic probe device of claim 1, wherein the spiral groove contains and allows the follower pillar to slide along the spiral groove.

7. The ultrasonic probe device of claim 1, wherein the arm slot limits the follower pillar to undergo a 1D linear movement along the arm slot.

8. The ultrasonic probe device of claim 1, wherein the spiral groove comprises a first end and a second end, the first end is adjacent to the pivotal hole, a spiral radius of the planar spiral track is gradually increased from the first end to the second end, and a length of the arm slot covers at least a length of the spiral groove in a radial direction from the center of the spiral groove to the second end of the spiral groove.

9. The ultrasonic probe device of claim 1, wherein the spiral-track plate is fixed to an inner wall of the sealed housing.

10. The ultrasonic probe device of claim 1, wherein the ultrasonic probe is to generate an ultrasonic-wave energy, the sealed housing is filled with a liquid medium, and the liquid medium is to promote transmission of the ultrasonic-wave energy.

11. The ultrasonic probe device of claim 1, further comprising:
motor, comprising a motor shaft; and
a shaft coupler, for connecting the motor shaft and the center shaft.

12. The ultrasonic probe device of claim 1, wherein the guide portion is located between the arm and the connection side.

13. The ultrasonic probe device of claim 1, wherein the guide portion is longer than the arm.

14. The ultrasonic probe device of claim 1, further comprising a cable connected to the detection side and extending along the leg portion.

15. The ultrasonic probe device of claim 14, wherein the leg portion is located outside of the spiral-track plate, the pivotal shaft serves as a rotating axis for the guide portion, and the guide portion swings with respect to the spiral-track plate.

16. An ultrasonic probe device of claim 1, further comprising:
a gear, adjacent to the spiral-track plate, having a first slot and a center gear hole;
wherein the arm, has one end thereof pivotally fixed to the sealed housing; and
wherein the center shaft, penetrates through the sealed housing, the pivotal hole of the spiral-track plate, and the center gear hole of the gear.

17. The ultrasonic probe device of claim 16, wherein the gear is located between the spiral-track plate and the arm.

18. The ultrasonic probe device of claim 16, wherein the pivotal hole is located at the center of the spiral-track plate, and the pivotal hole allows the center shaft to rotate with respect to the spiral-track plate.

19. The ultrasonic probe device of claim 16, further comprising a pinion meshing the gear, and the pinion is connected with a motor.

20. The ultrasonic probe device of claim 16, wherein the center gear hole is located at a center of the gear, the first slot is adjacent to the center gear hole, and the gear is fixed with the center shaft through the center gear hole.

21. The ultrasonic probe device of claim 16, wherein the first slot is extended outward from the center gear hole in a radial direction of the gear.

22. The ultrasonic probe device of claim 16, wherein the planar motion track defines 2D directional in-plane movements of the ultrasonic probe parallel to the spiral-track plate.

23. The ultrasonic probe device of claim 16, wherein the spiral groove contains and allows the follower pillar to slide therealong.

24. The ultrasonic probe device of claim 16, wherein the first slot of the gear limits the follower pillar to undergo a 1D linear movement along the first slot.

25. The ultrasonic probe device of claim 16, further comprising a pivotal shaft located outside of the spiral-track plate, wherein the pivotal shaft serves as a rotating axis for the arm to swing with respect to the spiral-track plate.

26. The ultrasonic probe device of claim 16, wherein the ultrasonic probe is to generate an ultrasonic-wave energy, the sealed housing is filled with a liquid medium, and the liquid medium is to promote transmission of the ultrasonic-wave energy.

27. The ultrasonic probe device of claim 16, wherein lengths of the arm slot and the first slot are different.

28. The ultrasonic probe device of claim 16, wherein the spiral-track plate is fixed to an inner wall of the sealed housing.

29. An ultrasonic probe device, comprising:
a sealed housing;
a spiral-track plate, disposed inside the sealed housing, comprising a pivotal hole and a spiral groove, the spiral groove being extended outward from a center of the spiral-track plate;
an arm, comprising an arm slot and an arm hole;
an ultrasonic probe, comprising a follower, a follower pillar, a detection side and a connection side opposing to the detection side, wherein the follower pillar of the ultrasonic probe connects to the connection side via penetrating through the arm slot in the arm and entering the spiral groove, and the spiral groove provides a planar motion track to the detection side of the ultrasonic probe;

a center shaft, penetrating through the sealed housing and the pivotal hole of the spiral-track plate; and an L-shape guide member, wherein the L-shape guide member comprises a leg portion and a guide portion having a guide slot, with one end of the leg portion, which serves as a pivotal shaft, affixed to the sealed housing, and another end of the leg portion connected to the guide portion, wherein the follower of the ultrasonic probe attaches to the connection side by penetrating through the guide slot in the guide portion, and wherein the guide slot of the guide portion and the arm slot of the arm have different widths.

30. The ultrasonic probe device of claim 29, wherein the the follower of the ultrasonic probe is located between the follower pillar and the connection side, and the guide slot contains and limits the follower to undergo a 1D linear movement along the guide slot.

\* \* \* \* \*